(12) United States Patent
Issadore et al.

(10) Patent No.: US 11,305,280 B2
(45) Date of Patent: *Apr. 19, 2022

(54) MAGNETIC SEPARATION FILTERS FOR MICROFLUIDIC DEVICES

(71) Applicant: The Trustees of the University of Pennsylvania, Philadelphia, PA (US)

(72) Inventors: David Aaron Issadore, Philadelphia, PA (US); Melaku Muluneh Woldemariam, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 231 days.

This patent is subject to a terminal disclaimer.

(21) Appl. No.: 16/411,284

(22) Filed: May 14, 2019

(65) Prior Publication Data
US 2019/0336973 A1 Nov. 7, 2019

Related U.S. Application Data

(63) Continuation of application No. 14/907,720, filed as application No. PCT/US2014/047745 on Jul. 23, 2014, now Pat. No. 10,335,789.
(Continued)

(51) Int. Cl.
*B01L 99/00* (2010.01)
*B03C 1/00* (2006.01)
*B01L 3/00* (2006.01)
*B03C 1/035* (2006.01)
*B03C 1/28* (2006.01)
(Continued)

(52) U.S. Cl.
CPC ........ *B01L 3/502753* (2013.01); *B03C 1/035* (2013.01); *B03C 1/288* (2013.01); *G01N 33/56911* (2013.01); *G01N 33/57484* (2013.01); *B01L 2200/0647* (2013.01);
(Continued)

(58) Field of Classification Search
None
See application file for complete search history.

(56) References Cited

U.S. PATENT DOCUMENTS 4,279,748 A 7/1981 Inoue
5,514,340 A * 5/1996 Lansdorp ................ B03C 1/286
422/534

(Continued)

FOREIGN PATENT DOCUMENTS

WO 2009/029859 A2 3/2009

OTHER PUBLICATIONS

Earhart et al., J. Magn Magn Mater, "Microfabricated magnetic sifter for high-throughput and high-gradient magnetic separation" National Institute of Health, May 2009, 321 (10), 1436-1439.
(Continued)

*Primary Examiner* — Paul S Hyun
(74) *Attorney, Agent, or Firm* — BakerHostetler

(57) ABSTRACT

A magnetic separation device has a membrane having a plurality of pores, a magnetically soft material layer disposed on the membrane, and a passivation layer disposed on the magnetically soft material layer. The magnetic separation device may be part of a microfluidic device having a lateral flow channel and a vertical flow magnetic separation filter. The magnetic separation device may be used to separate magnetically tagged particles, such as cells.

23 Claims, 13 Drawing Sheets

Related U.S. Application Data

(60) Provisional application No. 61/858,883, filed on Jul. 26, 2013.

(51) Int. Cl.
  *G01N 33/569* (2006.01)
  *G01N 33/574* (2006.01)
(52) U.S. Cl.
  CPC ... *B01L 2300/06* (2013.01); *B01L 2300/0681* (2013.01); *B03C 2201/18* (2013.01); *B03C 2201/26* (2013.01)

(56) References Cited

U.S. PATENT DOCUMENTS

| | | |
|---|---|---|
| 7,892,427 B2 | 2/2011 | Barbic et al. |
| 2002/0068187 A1 | 6/2002 | O'Connor et al. |
| 2004/0226884 A1 | 11/2004 | O'Connor et al. |
| 2005/0148064 A1 | 7/2005 | Yamakawa et al. |
| 2006/0234582 A1 | 10/2006 | Gohl et al. |

OTHER PUBLICATIONS

International Preliminary Report on Patentability for International Application No. PCT/US2014/047745 dated Jan. 26, 2016.
International Search Report for International Application No. PCT/US14/47745 dated Nov. 5, 2014.
Written Opinion of the International Searching Authority for International Application No. PCT/US4775 dated Nov. 5, 2014.

\* cited by examiner

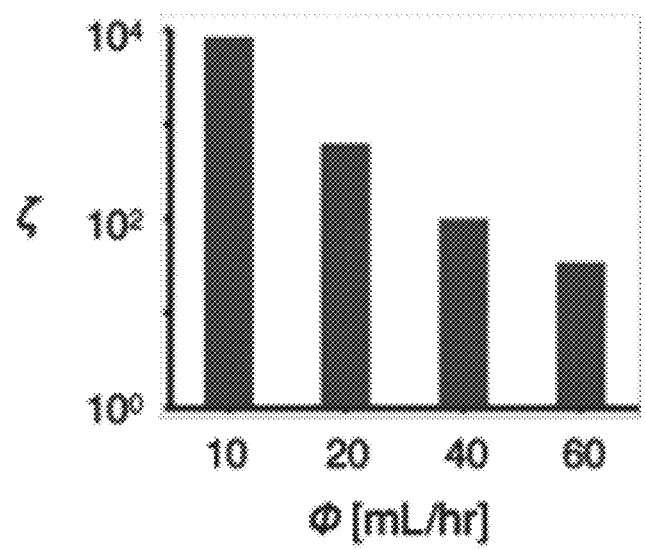
FIG. 3C
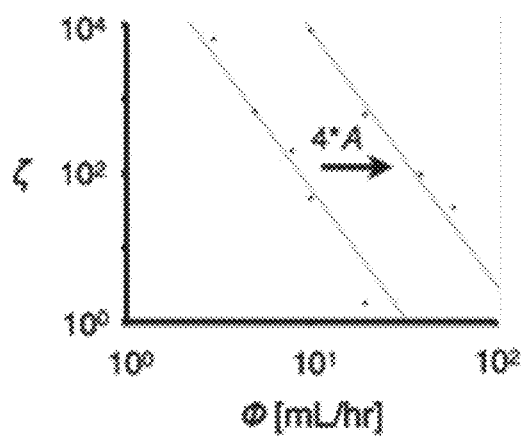
FIG. 3D

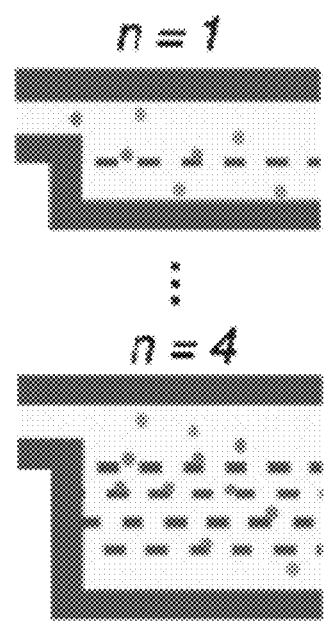
FIG. 4A
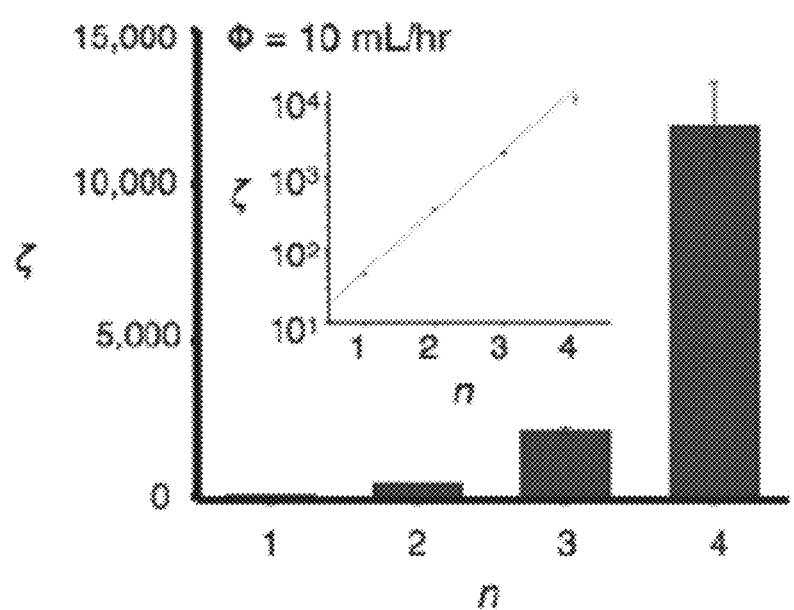
FIG. 4B

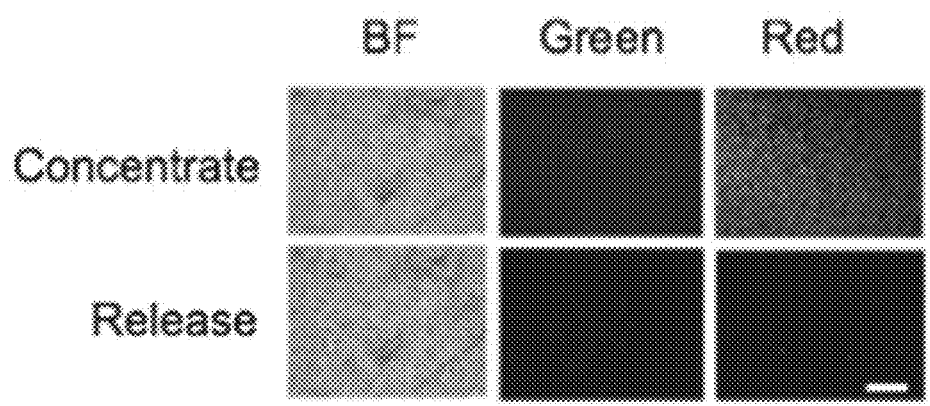
FIG. 5D
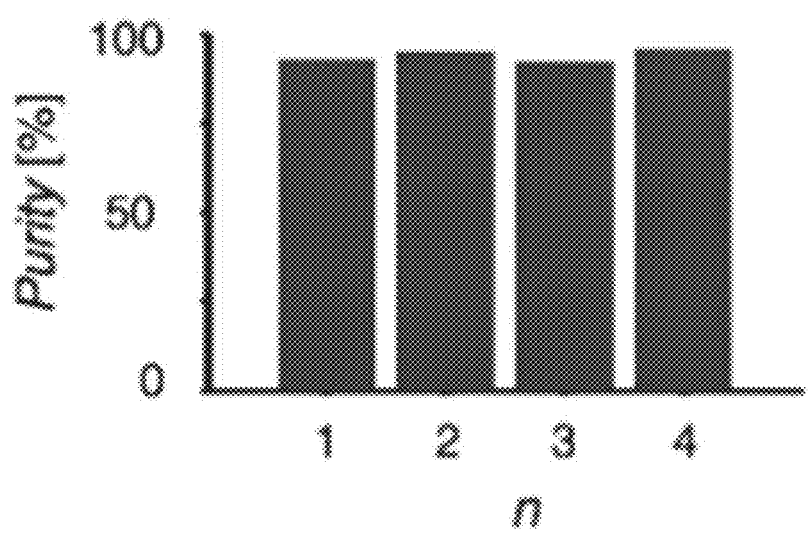
FIG. 5E

MAGNETIC SEPARATION FILTERS FOR MICROFLUIDIC DEVICES

CROSS REFERENCE TO RELATED APPLICATIONS

This application is a continuation of now-allowed U.S. application Ser. No. 14/907,720, filed Jan. 26, 2016, which is the U.S. National Phase application of PCT International Application No. PCT/US2014/047745, filed Jul. 23, 2014, which is related to and claims the benefit of U.S. Provisional Application No. 61/858,883, entitled "MAGNETIC SEPARATION FILTERS AND MICROFLUIDIC DEVICES USING MAGNETIC SEPARATION FILTERS" filed 26 Jul. 2013, the contents of which foregoing applications are incorporated herein by reference in their entireties and for all purposes.

FIELD OF THE INVENTION

The present invention relates to magnetic separation devices to selectively and rapidly sort objects. The present invention also relates to microfluidic devices comprising magnetic separation devices and methods for separating magnetically tagged objects.

BACKGROUND INFORMATION

The isolation of rare biological targets, such as circulating tumor cells (CTCs), pathogenic bacteria, or circulating microvesicles (CµVs), from easily accessible biological fluids is of great importance for disease monitoring and diagnostics. Detection platforms that utilize micro- and nanoscale structures, where dimensions can be designed to match those of the biological target, have been utilized for highly efficient and selective sorting. One method that has been particularly successful for isolating rare cells from clinical samples is magnetophoresis, in which immunomagnetically labeled targets are isolated from suspensions using strong and highly localized magnetic forces. Due to the lack of magnetic susceptibility of biological materials, magnetic sorting can be performed directly on unprocessed clinical samples (e.g., blood) and environmental samples (e.g., drinking water). Furthermore, strong forces can be applied without the need for a power supply or moving parts, making these devices well suited for use in practical settings outside of the laboratory.

Much work has been done to develop and improve magnetic isolation using microfabrication techniques. Micropatterned magnetic field profiles have been engineered using lithographically defined current carrying wires and paramagnetic materials. Additionally, a number of bottom-up fabrication strategies have been developed to create strong magnetic forces. Microfluidic channels have been used in conjunction with patterned magnetic fields to bring targeted cells close to the high magnetic field gradients, to provide predictable flow velocities, and to minimize non-magnetic retention.

Earhart et al. (J Magn Magn Mater, May 2009; 231(10): 1436-1439; doi: 10.1016/j.jmmm.2009.02.062) disclose a vertical flow micro-magnetic sorting device comprising a silicon nitride sifter formed on a silicon wafer. The sifter is slots of the silicon nitride micropores coated with the magnetic CoTaZr film, and magnetically labeled particles are captured in the slots.

There is a need for magnetic separation devices that have improved sorting efficiencies and/or greater throughput, which can be produced inexpensively and incorporated into microfluidic devices.

SUMMARY OF THE INVENTION

One aspect of the present invention relates to a flexible magnetic separation device comprising a membrane including a plurality of pores, wherein the pores have an average diameter ranging from about 100 nm to 100 µm, a layer of magnetically soft material adjacent said membrane, and a passivation layer adjacent said layer of magnetically soft material.

Another aspect of the present invention relates to a microfluidic device comprising at least one lateral flow channel and at least one vertical flow magnetic separation filter in fluidic communication with the at least one lateral flow channel, wherein the at least one vertical flow magnetic separation filter comprises a membrane comprising a plurality of pores, a layer of magnetically soft material disposed on said membrane, and a passivation layer disposed on said layer of magnetically soft material.

Yet another aspect of the present invention relates to a method for separating magnetically tagged particles in a microfluidic device, comprising exposing a vertical flow magnetic separation filter to an external magnetic field, wherein the vertical flow magnetic separation filter comprises a membrane comprising a plurality of pores, a layer of magnetically soft material disposed on the membrane, and a passivation layer disposed on the layer of magnetically soft material; flowing a suspension comprising the magnetically tagged particles through a lateral flow channel in a microfluidic device; capturing the magnetically tagged particles in the vertical flow magnetic separation filter; removing the external magnetic field; and releasing the captured magnetically tagged particles.

BRIEF DESCRIPTION OF THE DRAWINGS

FIG. 3C is a graph of enrichment, s, as a function of flow rate, θ.

FIG. 3D is a graph showing the effect of surface area on the enrichment, ξ as a function of flow rate, θ.

FIG. 4A shows schematic representations of a microfluidic device comprising a single vertical flow magnetic separation filter and a microfluidic device comprising four vertical flow magnetic separation filters connected in series.

FIG. 4B is a graph showing the effect of the number of vertical flow magnetic separation filters connected in series on the enrichment, s, as a function of the number of filters in series.

FIG. 5D is a fluorescence micrograph of cells on a vertical flow magnetic separation filter during capture and after release.

FIG. 5E is a graph of the purity of captured and released beads as a function of the number of vertical flow magnetic separation filters connected in series.

DETAILED DESCRIPTION OF THE INVENTION

Figure 1A:
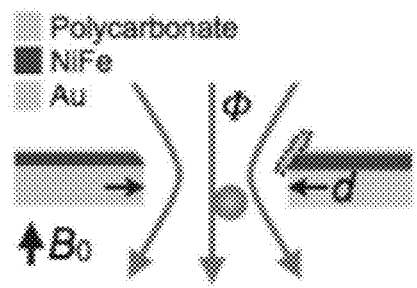
FIG. 1A is a schematic representation of a pore within a magnetic separation device.

One aspect of the present invention relates to a magnetic separation device, or filter. As used herein, the phrases "magnetic separation device" and "magnetic separation filter" are used interchangeably to refer to a device through which material flows, and which magnetically captures targeted objects. The targeted objects may be magnetically tagged objects, such as, for example, cells, molecules, nucleic acids, proteins, etc.

According to at least one embodiment, the magnetic separation device comprises a membrane having a plurality of pores, a layer comprising a magnetically soft material, and a passivation layer.

As used herein, the terms "pore" and "micropore" are used interchangeably to refer to channels that pass completely through the membrane, i.e., continuous channels that pass from one surface of the membrane to the opposite surface of the membrane. FIG. 1D shows SEM micrographs of the pores of a magnetic separation device with scale bars (from left to right) of 2 μm, 25 μm, and 200 μm.

In at least one embodiment, the membrane is a material chosen from cellulosic, polymers, and metal oxide films. Examples of materials that may be used include, but are not limited to, paper, polycarbonate, polyester, nylon, and aluminum oxide. In at least one embodiment, the membrane is polycarbonate.

According to at least one embodiment, the membrane is composed of a material capable of being ion track etched. Ion track-etching can be used to provide uniform pore sizes in the membrane material. Pores formed by ion track-etching are typically randomly arranged in the film. A magnetic separation device comprising ion track-etched pores is referred to herein as a Track-Etched Magnetic micro-Pore (TEMPO) device or filter, which are used in various embodiments and examples used throughout the present disclosure. Other methods of forming pores within membranes known in the art can also be used. The magnetic separation device of the present invention, however, is not intended to be limited to ion track-etched devices and one skilled in the art will recognize that unless otherwise specified, embodiments which refer to TEMPO filters may include magnetic separation devices formed by other methods. In at least one embodiment, the membrane is ion track-etched polycarbonate.

The magnetic separation device may be flexible. Flexibility of the magnetic separation device can be beneficial in the construction of microfluidic devices. Rigid devices, such as those constructed of silicon, may be difficult to manipulate within the confines of small structures, such as those found in microfluidic devices.

In at least one embodiment, the membrane comprises a pores at a pore density of at least 1000 pores/mm$^2$, such as, for example, at least 1500 pores/mm$^2$, at least 2000 pores/mm$^2$, or more.

The pores may have an average diameter ranging from about 100 nm to about 100 μm, such as, for example, from about 100 nm to about 50 μm, from about 500 nm to about 50 μm, from about 500 nm to about 25 μm, or from about 500 nm to about 10 μm. In at least one embodiment, the pores have an average diameter less than about 50 μm, such as, for example, less than about 25 μm, less than 10 μm, less than about 5 μm, less than about 2 μm, or less than about 1 μm. As one skilled in the art would recognize, the size of the pores may be selected based on the size of the objects being separated. In at least one embodiment, the size of the pores is selected such that the pores are large enough not to trap the objects, but small enough to expose the objects to the greatest magnetic field gradient possible. For example, when a suspension comprises particles that are 1 μm in diameter, the pore size may be 4 μm in diameter. In at least one embodiment, the pore size is about 2 to 5 times the size of the target object.

The pores within the membrane may have any cross-sectional shape, such as, for example, circular, oval, rectangular, square, or other polygonal shape.

The pore shape influences the magnetic field gradient. In at least one embodiment, the pores have a symmetrical geometry. According to at least one embodiment, the pores have a circular cross-section. Without wishing to be limited by theory, it is believed that a circular cross-section provides the most uniform magnetic field gradient.

The layer of magnetically soft material in the magnetic separation device may comprise a material selected based on its magnetic properties.

As used herein, the phrase "magnetically soft material" refers to a material which can become magnetized by a relatively low-strength, external magnetic field, e.g., by a magnet placed in close proximity to the material, that returns to a state of relatively low residual magnetism when the external magnetic field is removed.

In at least one embodiment, the magnetically soft material is capable of having an induced magnetic field when an external magnetic field is applied. The magnetically soft material may also be selected based on the magnetic remanence, i.e., the materials ability to return to a non-magnetic state when the external magnetic field is removed.

In at least one embodiment, the magnetically soft material is selected from permalloys, which include allows of nickel and iron. In accordance with at least one embodiment, the magnetically soft material is Ni$_{20}$Fe$_{80}$, an alloy which comprises 20% nickel and 80% iron.

The passivation layer of the magnetic separation device may protect the magnetically soft material from undesired interaction or reaction with fluids that the magnetic separation device may come in contact with. For example, the passivation layer may protect the magnetically soft material from oxidation. In at least one embodiment, the passivation layer is comprised of a material chosen from inert materials, such as, for example, gold or nickel.

The magnetically soft material and the passivation layer may be formed on the membrane using any technique known in the art. For example, the materials may be deposited by thermal evaporation, sputtering, chemical vapor deposition, electroplating, etc.

In at least one embodiment, the membrane comprises a commercially available ion track-etched polycarbonate membrane. The membrane is coated with a thin layer of magnetically soft material (e.g., permalloy) and a passivation layer of gold.

Polycarbonate membranes can be track-etched with pore sizes ranging from 100 nm to 100 μm over large areas (A>10 cm$^2$) for little cost (<$0.05/cm$^2$). The membranes are flexible and can be integrated into laminate sheet microfluidics patterned with laser micromachining. Due to the large size of the membranes (A>1 cm$^2$), highly efficient isolation ($\xi$>10$^4$) can be achieved at extremely high flow rates ($\theta$>10 ml/hr). Without wishing to be limited by theory, it is believed that there are three main elements of the magnetic separation filter which maximize the magnetic force $F_m$ and minimize the drag force $F_d$ on targeted cells, and thus optimize the sorting efficiency of the filter.

Strong magnetic field with high field gradient (B↑, ∇B↑). The magnetic force $F_m$~(B·∇)B can be maximized by increasing the strength of the applied field B and its spatial changes ∇B. The magnetic separation filter generates strong fields (|B|=0.2 T) due to the external magnet and strong, highly localized magnetic field gradients due to the micropore geometry (FIG. 2A), to create strong magnetic trapping forces.

Large flow channel area (v). The hydrodynamic drag force $F_d$=6πμav, where μ is the viscosity and v is the fluidic velocity, can be minimized by using columnar flow instead of low that is in-plane with a 1 in$^3$ NdFeB magnet (FIG. 1B). The cross sectional area of a vertical glow channel grows quadratically with the dimensions of the chip L$^2$, rather than linearly as with lateral flow. This feature may allow large flow rates $\theta$ to be obtained, while keeping the flow velocity v small and the chip compact. Utilizing this approach, efficient sorting can be achieved at very high flow rates ($\theta$>10 ml/hr). Close proximity of each cell to the regions of strong magnetic force (r↓). Because each cell must pass through a micropore, each cell comes within r=d/2 of the edge of the pore, where d is the micropore diameter and the micropore has a circular cross-section. By choosing the pore size to be on the same size-scale as the object being trapped, it can be ensured that each cell comes within close proximity of the high-force trapping region.

Another aspect of the present disclosure relates to a microfluidic device comprising a magnetic separation device.

In at least one embodiment, the microfluidic device comprises at least one lateral flow channel and at least one vertical flow magnetic separation filter. The vertical flow magnetic separation filter, such as, for example, a TEMPO filter, which comprises a membrane having a plurality of pores, a layer of magnetically soft material disposed on the membrane, and a passivation layer disposed on the layer of magnetically soft material.

The microfluidic device may comprise any known structural or functional element. In at least one embodiment, the microfluidic device can be modular, including the vertical flow magnetic separation filter.

In at least one embodiment, the microfluidic device comprises a plurality of vertical flow magnetic separation filters. Because each additional vertical flow magnetic separation filter increases the enrichment, one of ordinary skill in the art would recognize that the number of vertical flow magnetic separation filters can be selected to achieve the desired level of enrichment. In at least one embodiment, the microfluidic device comprises from 2 to 10 vertical flow magnetic separation filters, such as, for example, from 2 to 4. In other embodiments, the microfluidic device could contain more than 10 vertical flow magnetic separation filters.

The plurality of vertical flow magnetic separation filters can be arranged in series. In at least one embodiment, each of the plurality of vertical flow magnetic separation filters has a membrane containing pores and a pore density that are similar. In other embodiments, each of the vertical flow magnetic separation filters may comprise membranes having different pore sizes and/or pore densities.

According to at least one embodiment, the microfluidic device may comprise a flow converter for redirecting the lateral flow in the at least one lateral flow channel to vertical flow in the at least one vertical flow magnetic separation filter. The flow converter may comprise, for example, a plurality of pathways through which fluid can pass from the lateral flow channel to the vertical flow magnetic separation filter. Each of the plurality of pathways, for example, may be of similar length, such that fluid passing through the microfluidic device will have the same residence time regardless of the path through which the fluid flows. In at least one embodiment, the flow converter comprises a symmetric branched geometry.

A microfluidic device according to an embodiment of the present disclosure is shown in FIG. 1E. The microfluidic device comprises an acrylic substrate, a lower 200 μm mylar layer, a TEMPO filter, a flow converter comprising a layer of 50 μm mylar film having 16 regularly spaced holes and a layer of 200 μm mylar film having a symmetric branched geometry in fluidic communication with the 16 regularly spaced holes and fed by a lateral flow channel, and a top layer of 50 μm mylar film.

Another aspect of the present disclosure relates to a method for separating magnetically tagged particles in a microfluidic device.

In at least one embodiment, the method comprises exposing a vertical flow magnetic separation filter to an external magnetic field to induce a magnetic field gradient within pores of a membrane in the vertical flow magnetic separation filter, flowing a suspension comprising magnetically tagged particles through a lateral flow channel in a microfluidic device, capturing the magnetically tagged particles in the pores of the vertical flow magnetic separation filter, removing the external magnetic field, and releasing the captured magnetically tagged particles.

The magnetically tagged particles may comprise, for example, cells, molecules, nucleic acids, proteins, polypeptides, or another taggable object of interest.

Examples

To demonstrate the utility of this platform, a chip with a 5 μm pore size TEMPO was used to efficiently isolate immunomagnetically labeled *E. Coli* from a suspension of similarly sized bacteria for subsequent downstream analysis.

Figure 1B:
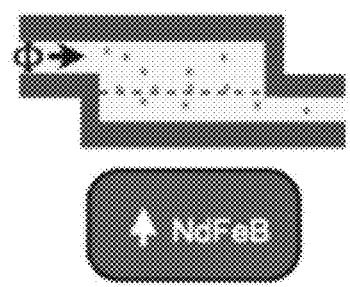
FIG. 1B is a schematic representation of a microfluidic device comprising a vertical flow magnetic separation filter.

The TEMPO filter comprises a dense array (2000/mm$^2$) of track-etched micropores coated with a thin layer of soft magnetic material (FIG. 1A). The micropores create large gradients $\nabla B$, which imparts strong magnetic forces $F\sim(B\cdot\nabla)B$ on magnetic nanoparticle *MNP labeled cells as they pass through the pores. Targeted cells are trapped and isolated from the unlabeled cells which flow through the filter unimpeded. The chip sits in a large uniform magnetic field $|B|=0.2$ T, provided by a small external neodymium iron boron (NdFeB) magnet. This field magnetized both the MNP labeled cells and the TEMPO filter. When the NdFeB magnet is removed, the force disappears and the trapped cells can be efficiently released.

Microfluidic Chip

Figure 1C:
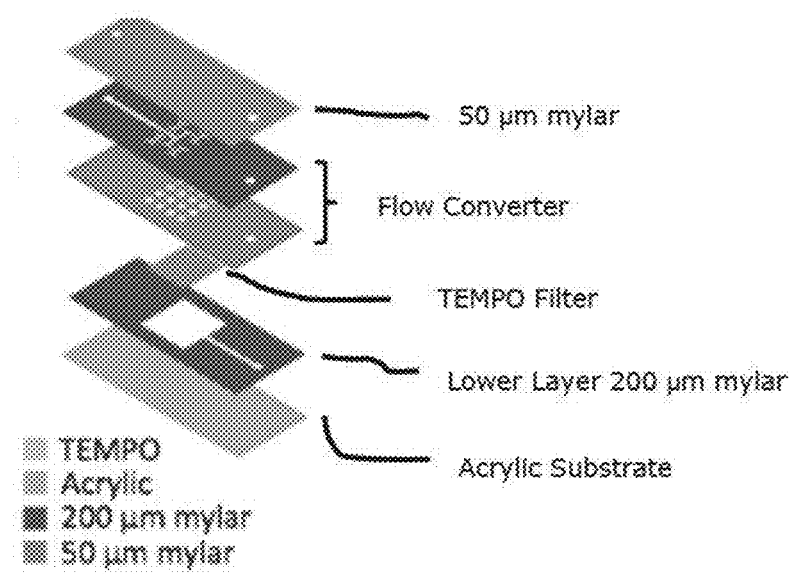
FIG. 1C is an exploded view of a microfluidic device comprising a vertical flow magnetic separation filter.
Figure 1D:
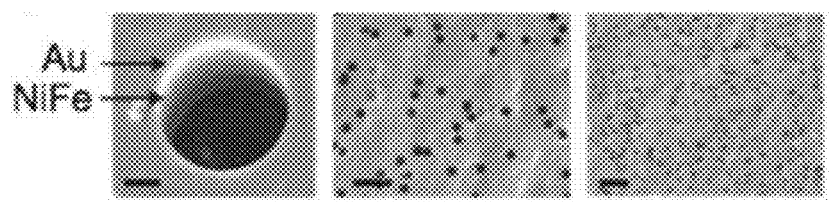
FIG. 1D is a series of SEM micrographs of a magnetic separation device at different magnifications.

A microfluidic chip was fabricated by integrating the TEMPO filter into a microfluidic network. To fabricate the TEMPO filter, flexible track etched films (Whatman Nuclepore) were coated with soft magnetic material (200 nm, $Ni_{20}Fe_{80}$) and a passivation layer (30 nm, Au) using thermal evaporation. The metals are thermally evaporated using a Kurt Lesker (PVD-75) e-beam/thermal evaporator in the Wolf Nanofabrication Facility at University of Pennsylvania. FIG. 1D shows an SEM micrograph of a 5 μm diameter 30 micropore TEMPO filter, with the gold, $Ni_{20}Fe_{80}$, and polycarbonate layers visible. The TEMPO filter was integrated into laser-cut laminate sheet microfluidics (FIG. 1C). The microfluidic chip was designed to evenly distribute fluid to the TEMPO filter, such that optimum sorting efficiency can be achieved. A "shower head" geometry was utilized (FIG. 1C), in which flow in a lateral microchannel was converted into an evenly distributed vertical flow. The flow was split evenly to sixteen 0.5 mm$^2$ holes above the TEMPO filter using a symmetric branching geometry. Underneath the TEMPO filter was a thick (200 μm) channel that brought the fluid to the output. The microfluidic channel patterns were defined using laser-cutting (VLS3, VersaLaser). The base was constructed using 1.5 mm thick extruded poly(methyl methacrylate) sheet (McMaster Carr). The device was coupled to blunt syringe tips (McMaster Carr) epoxied onto the top layer of the microfluidic chip to control flow through the chip. The device was pre-treated with Pluronic F-127 (Sigma-Aldrich) to minimize non-specific retention of cells to the channel walls or to the TEMPO filter.

Immunomagnetic Labeling of Bacteria

To demonstrate the utility of the TEMPO filter, immunomagnetically labeled bacteria were efficiently sorted from a heterogeneous suspension. An indirect labeling method was utilized in which the bacteria were first targeted with biotinylated antibody and subsequently tagged with anti-biotin MNPs. Nuclear Magnetic Resonance (NMR) measurements (Bruker Minispec) on the labeled cells revealed that there were 2300 particles per cell.

The samples were prepared mixing a known quantity of *E. coli* and *S. aureus*. Fresh *E. coli* bacteria samples (Invitrogen) were grown overnight in Luria-Bertain (LB) broth (10 g of tryptone, 5 g of yeast extract, and 10 g of NaCl/L) at 37° C. in 14 ml round-bottom tubes with rotary shaking for about 6 hours. The concentrations of the *E. coli* bacteria stock solutions were quantified by a Varian Cary 100 Bio UV-Visible Spectrophotometer. The cells were harvested at a concentration equivalent to an optical density at 600 nm value of 0.73 ($\sim 7$ $0.3\times 10^8$ cell/ml). The bacterial cells were then used for further experiments immediately.

The following steps were taken to magnetically label the cells. The *E. coli* stock sample was diluted to concentration range of $1\times10^7$-$9\times10^7$ cell/ml with buffer (0.5% bovine serum albumin and 2 mM EDTA in phosphate-buffered saline, Fisher Scientific). *S. aureus* pre-labeled with Alexa Fluor 594 were utilized. Biotinylated anti-*E. coli* polyclonal antibody (80 μl, 3.2 mg/ml, Thermo Scientific) and the diluted *E. coli* bacterial sample (80 μl, $1\times10^7$-$9\times10^7$ cell/ml) were mixed and incubated at room temperature for 1 hour. After that, the sample was washed twice by the buffer. Antibiotin nanoparticles (20 μl, Miltenyi Biotec) were added into the sample and incubated 30 at 4° C. for 15 minutes. The sample was subsequently centrifuged at 1100 ref for 10 minutes. The bacteria pellet was resuspended in 500 μl buffer. Unlabeled *E. coli* bacteria samples were set as a control. The nanoparticle conjugated bacteria sample and a control were measured by a Bruker Minispec MQ60 NMR analyzer to quantify labeling. For fluorescence detection, SYTO9 stain (500 ml, 10 μM, Life Technologies) was added into the nanoparticle conjugated bacteria sample and 15 minutes room temperature incubation was allowed. The sample was then washed 3 times with PBS to remove residual stain.

Characterization

Finite Element Simulations

Figure 2A:
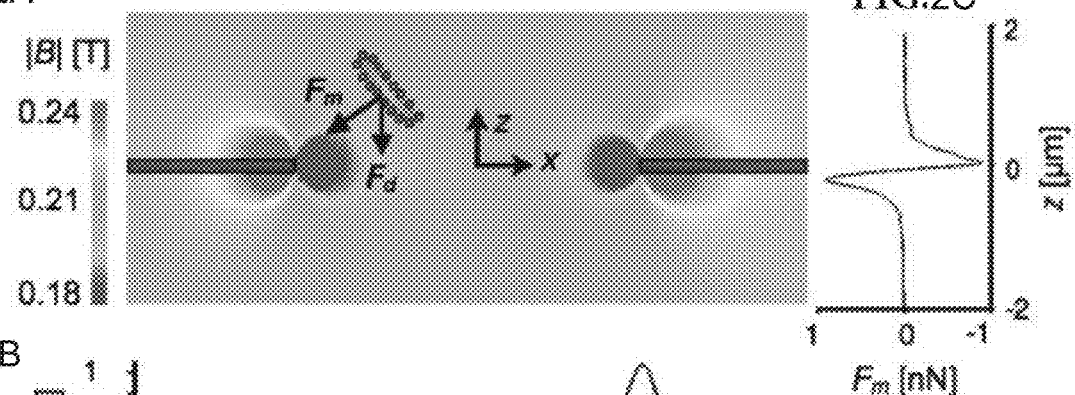
FIG. 2A provides a graphical representation of a magnetic field simulation of a pore within a magnetic separation device.

Magnetic field simulations were used to aid the design and characterization of the TEMPO filter. The simulated magnetic field strength B is plotted on the cross-section of the self-assembled magnetic filter (FIG. 2A). The magnetic field strength drops rapidly in distance from the surface of the magnetic layer, creating large gradients that least to strong magnetic forces. The simulation geometry was an axially symmetric membrane with a 5 μm pore, coated with 200 nm of $Ni_{20}Fe_{80}$. One inch below the TEMPO filter was a fully magnetized NdFeB magnet $M_p=875$ kA/m. Finite element simulations (Maxwell, Anson) were used to simulate the magnetic field B, from which the magnetic force $F_m$ was calculated.

Figure 2C:
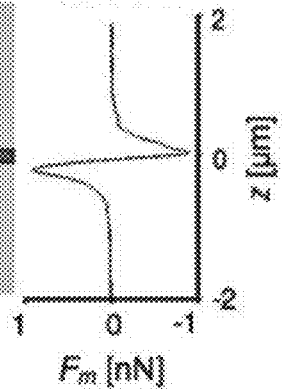
FIG. 2C provides the magnetic trapping force plotted against z Δx−500 nm from the edge of a micropore.
Figure 2B:
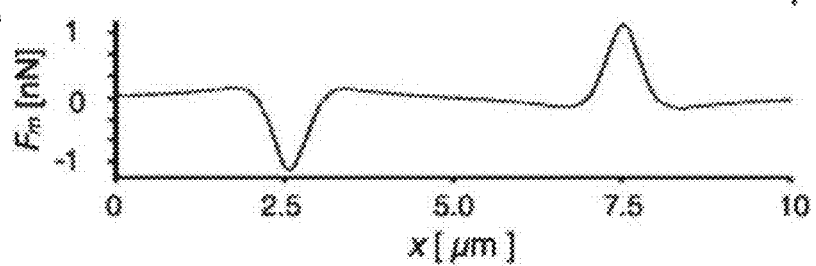
FIG. 2B provides the magnetic force on a 1 µm diameter magnetic microbead plotted as a function of x Δz=500 nm above a magnetic separation device.

The magnetophoretic force Fm on cells is calculated by combining the finite element simulation from FIG. 2A with the magnetic model described above. FIG. 2B shows the force that a 1 μm diameter iron oxide loaded bead experiences versus the lateral distance from the pore's edge, 500 nm above the TEMPO filter surface. The simulation shows that the force is localized within $\sim 2$ μm of the pore's edge. The ability of the pore to capture passing cells is therefore optimized when the pore diameter is as small as possible, while still being large enough to pass non-targeted objects.

Once a cell is brought to the edge of the pore, the competition of the magnetic trap and the drag force from the passing fluid determine whether the cell gets trapped. The drag force is given by Stokes' law ($F_d=6\pi\mu av$, where $\mu=0.8$ mPa*s is the viscosity of water. The average velocity can be calculated through the pores $V_{avg}=\Theta/(pA_pA)$ where $p=10^6$ pores/cm$^2$ is the pore density (Whatman), $A_p$ is the cross sectional area of an individual pore, and $A=0.39$ cm$^2$ is the cross-sectional area of the membrane. The flow profile through a single pore $v\propto(1-(1)-(r/a)^2)^{1/2}$ can be calculated based on the Stokes' equations of motion. The flow velocity is greatest in the center of the pore, and therefore the drag force $F_d$ is minimal at the edges of the pore where the cells are trapped. The magnetic force $F_m$ in the z direction that resists the flow is shown in FIG. 2C. A line was it to the force curve in FIB. 2B and the effective spring constant of the trap is found to be k=12.3 nN/μm. Once trapped, a 1 μm magnetic bead as modeled above, will remain trapped at flow rates $\theta > 100$ ml/hr.

Experimental Characterization

Figure 3A:
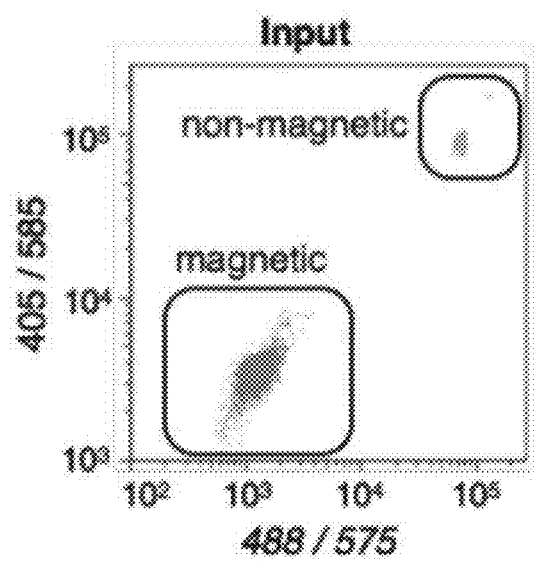
FIG. 3A is a flow cytometry quantification of bead population before filtration.
Figure 3B:
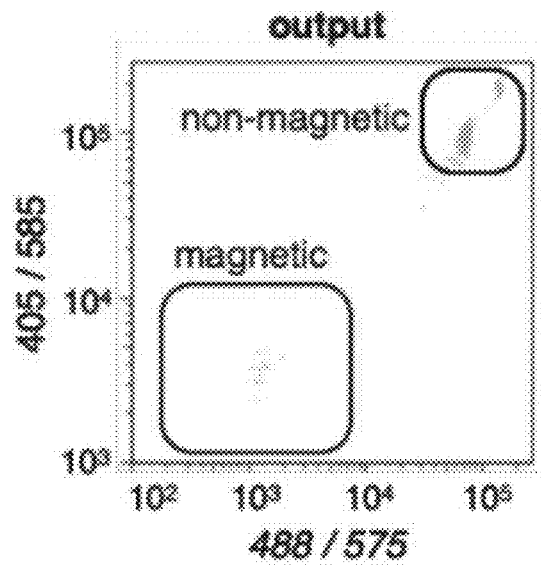
FIG. 3B is a flow cytometry quantification of bead population after filtration.

The efficiency of the TEMPO filter was first tested by sorting magnetic from nonmagnetic polystyrene beads. A suspension that contained both 1 μm diameter fluorescent polystyrene beads (FluoSpheres® Polystyrene Microspheres, 1.0 µm, Invitrogen) and 1 µm diameter fluorescent magnetic beads (screenMAG, Chemicell) was pumped through the TEMPO filter. The input (FIG. 3A) and output (FIG. 3B) were measured using flow cytometry (LSR II, BD), and the efficiency of the TEMPO filter was analyzed. The three parameters of the magnetic sorting device that were characterized include enrichment $\xi=(C_{1p}/C_{1m})/(C_{op}/C_{om})$, purity $C_{om}/C_{op}$, and flow rate θ), where $C_{op}$ and $C_{1p}$ are the concentration of non-targeted cells before and after sorting, respectively, and $C_{om}$ and $C_{1m}$ are the concentration of targeted cells before and after sorting, respectively.

The TEMPO filter achieved high sorting efficiency at flow rates as great as 60 L/hr (FIG. 3C). The sorting efficiency was observed to be a function of flow rate, following a power law dependency, $\phi \propto \xi^m$), where m=−3.74 ($R^2$=99.9%) over several orders of magnitude. By increasing the area of the filter from A=0.6×0.6 $cm^2$ to an area 4 times larger, the enrichment curve shifted to the right in flow rate θ by an amount linearly proportional to the increase in A (FIG. 3D). The power law shifted, but its slope m remained the same, suggesting that the power law dependency comes from an intrinsic property of the micropore geometry. The scaling of the flow rate θ with the area A of the filter, allows chips to be designed with a large range of flow rates appropriate for specific applications.

To further increase enrichment, several TEMPO filters can be placed in series. The TEMPO filters are placed in series by being stacked vertically, utilizing a slight modification to the fabrication strategy that is used for the single filter devices. There is one layer of 200 µm thick laser cut mylar between each TEMPO filter. Additional flow splitters are not necessary for each TEMPO layer, as the flow remains evenly distributed as it passes through the vertically integrated filters.

There is an exponential increase observed in sorting efficiency for each additional TEMPO filter (FIG. 4A). The exponential increase is understood by assuming that each filter enriches its input by an amount so, independent of any of the other filters. If each subsequent filter receives the previous filter's output as its input, then the enrichment after n stages is $\xi=(\xi_0)^N$. To test this effect, the enrichments of four different chips, with n=1, 2, 3, and 4 filters was measured (FIG. 4B). The enrichments fits well to an exponential $\xi \propto e^{bn}$, with b=1.84 ($R^2$=99.8%). This exponential growth allows for 30 large improvements in enrichment to be made by adding additional filters. For instance, by increasing n=1 to n=4 for an A=0.36 $cm^2$ TEMPO at θ=10 ml/hr, enrichment was improved 250×.

Figure 5A:
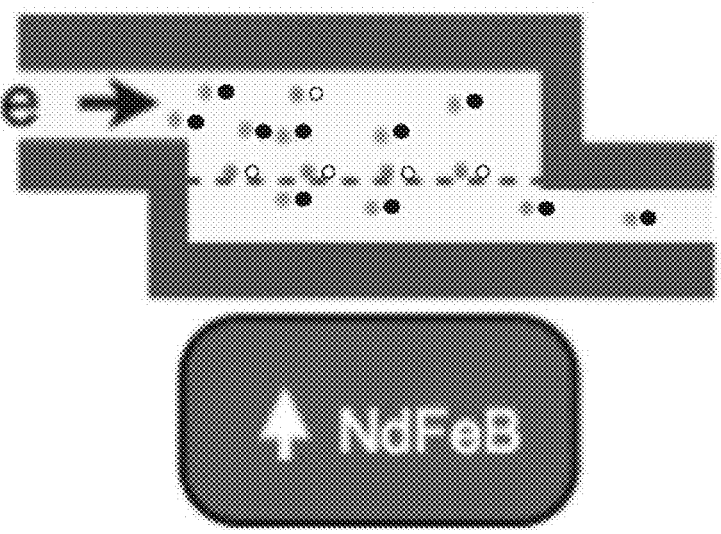
FIG. 5A-5C is a schematic representation of the trapping and releasing of magnetically tagged particles in a microfluidic device comprising a vertical flow magnetic separation filter.
Figure 5B:
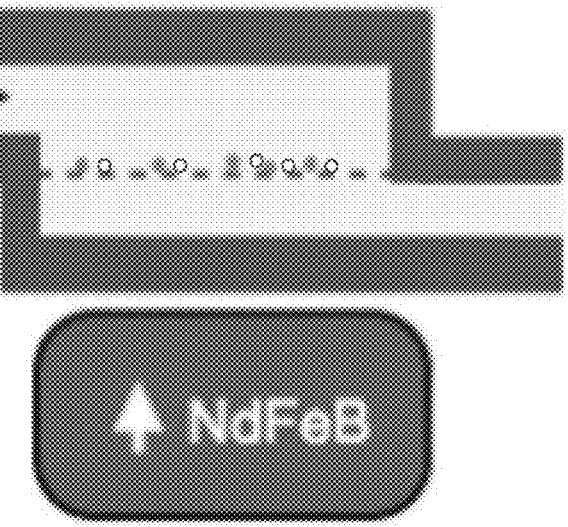
Figure 5C:
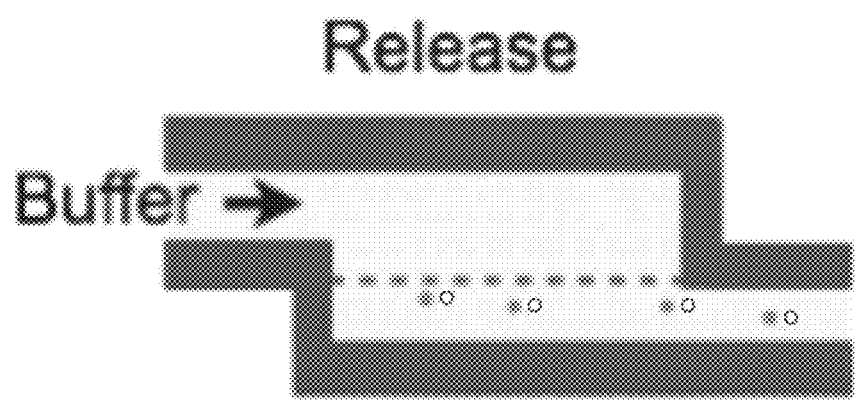

Release of cells is important for applications where downstream analysis is desired on whole cells, such as immunostaining or single cell genotyping. The TEMPO filter has the advantage that when the external magnet is removed, the magnetic force disappears and the trapped cells can be released. This feature is facilitated by the low magnetic remanence of $Ni_{20}Fe_{80}$, which brings the magnetization to zero when the external magnet is taken away. The trap and release protocol is outlined in FIG. 5. First, the targeted cells (open circles ○) are trapped and concentrated by passing the sample through the TEMPO filter with the external magnet in place (FIG. 5A). Next, cells and debris (closed circles •) that were not trapped are washed away by passing buffer solution through the TEMPO filter with the external magnet still in place (FIG. 5B). Finally, the external magnet is removed and the trapped cells are released into the passing buffer solution (FIG. 5C). To demonstrate this functionality, magnetic beads were trapped from a suspension of non-magnetic beads, washed, and then subsequently released (FIG. 5D). The purity of the output of the release beads was quantitatively measured (>95%) and did not significantly change with additional layers of TEMPO (P>0.5, two-tailed t test) (FIG. 5E).

Figure 6A:
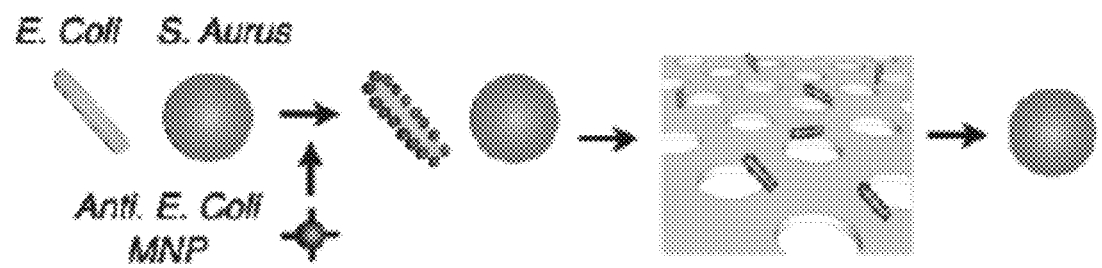
FIG. 6A is a schematic representation depicting the capture of magnetically tagged bacteria by a vertical flow magnetic separation filter.
Figure 6B:
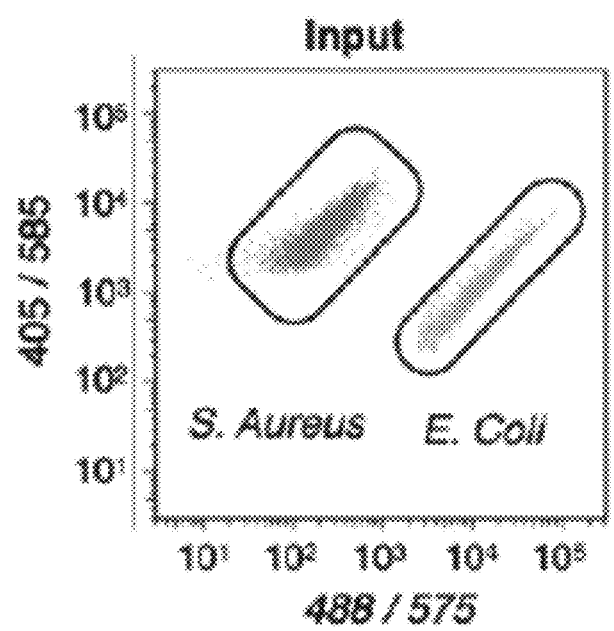
FIG. 6B is a flow cytometry quantification of cell population before filtration.
Figure 6C:
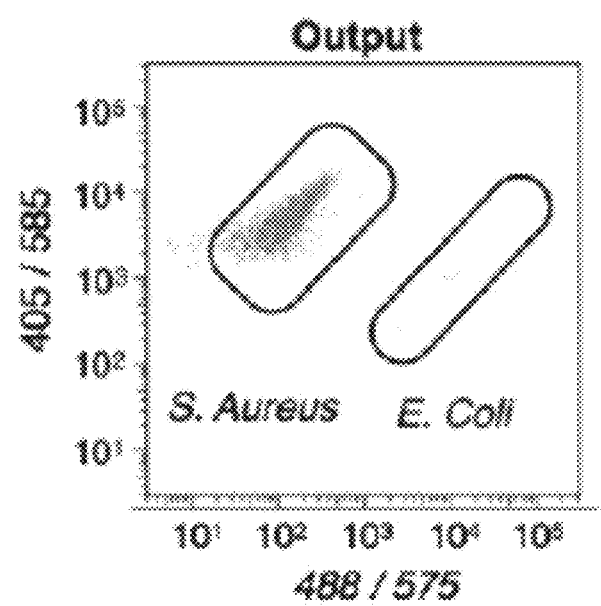
FIG. 6C is a flow cytometry quantification of cell population after filtration.

The ability of the TEMPO filter to sort bacterial cells was demonstrated by magnetically capturing *E. coli* bacteria from a suspension of *S. Aureus*, based on an anti-*E. coli* antibody (FIG. 6A-6C). A TEMPO with n=3 filters and an area A=0.6×0.6 $cm^2$ was used. The change in the composition of the suspension before and after filtration was measured by flow cytometry. The input (FIG. 6B) and output (FIG. 6C) were measured using flow cytometry, and the sorting efficiency of the TEMPO was analyzed. At a flow rate of θ=1 ml/hr, enrichment of $\xi$=450 was achieved. Flow rates and enrichment rates could be increased further by enlarging the area of the filter A or the number of 20 filters n, as was shown above.

Background Insensitivity

To demonstrate background insensitivity, prepared *E. coli* and *S. aureus* samples were spiked into multiple samples (phosphate buffer saline (PBS), PBS with excess MNPs ($10^8$/ml), oral lavage from a healthy volunteer, and local river water). The oral lavage was collected by having a healthy volunteer rinse his mouth for 30 s with sterile saline solution. The river water was collected from the Schuykill River in Philadelphia, Pa. For each test, 1 ml of each sample was spiked with $8×10^5$ *E. coli* and $6×10^4$ *S. aureus*.

Oral lavage is commonly used for the diagnosis of oral infections, and samples include a heterogeneous suspension of bacteria including *A. actinomycetemcomitans* (Aa), *P. gingivalis* (Pg), *T. forsythensis* (Tf), *P. intermedia* (Pi), and *M. micros* (Mm). The observed enrichment<; from oral lavage and in PBS was statistically identical (P>0.5, a two-tailed t-test), verigying that the complex background of the clinical samples had a negligible effect on TEMPO sorting. Further comparisons were made on samples with excess MNPs ($10^8$ particles per ml) and on an environmental sample from the Schuykill River. In both cases, the measured enrichment was found to be statistically identical (P>0.5, a two-tailed t-test) to that measured in PBS.

Figure 6D:
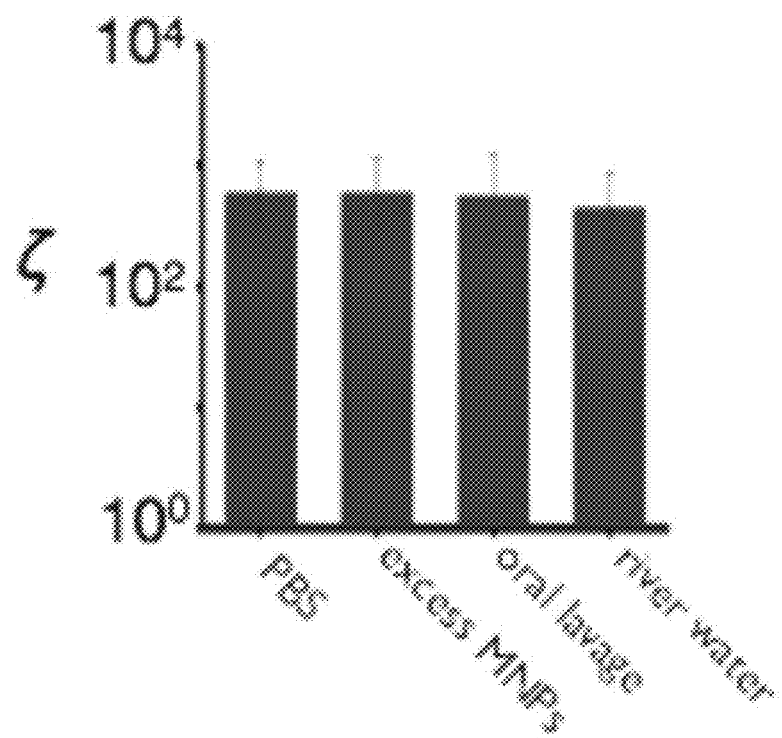
FIG. 6D is a graph comparing the enrichment for various samples.

Both the clinical and environmental sample contained particulates larger than the pore size of the TEMPO (d=5 µm). However, due to the large density of micropores (p=$10^6$ $cm^{-2}$), the blockage of a few pores did not significantly change the behavior of the device. Additionally, due to the use of magnetic sorting, the MNP-labeled cell could be sorted directly from the unprocessed clinical and environmental sample without interference from salinity, turbidity, or pH. FIG. 6D shows the enrichment for each of the samples.

Separation of Circulating Tumor Cells (CTCs)

Figure 7A:
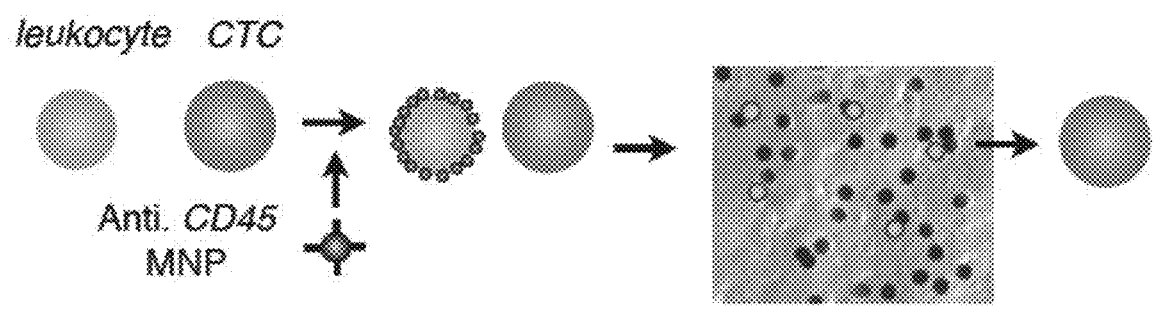
FIG. 7A is a schematic representation depicting the capture of magnetically labeled circulating tumor cells by a vertical flow magnetic separation filter.
Figure 7B:
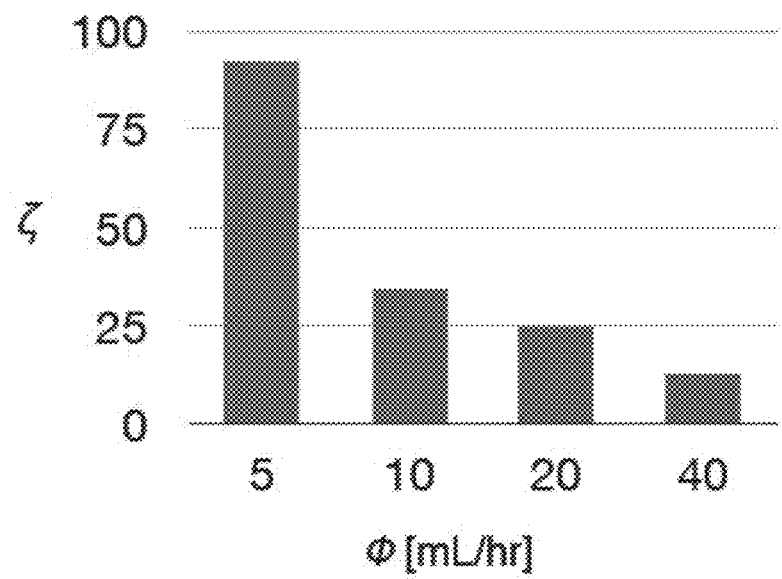
FIG. 7B is a graph of enrichment $\xi$, as a function of flow rate, $\theta$.
Figure 7C:
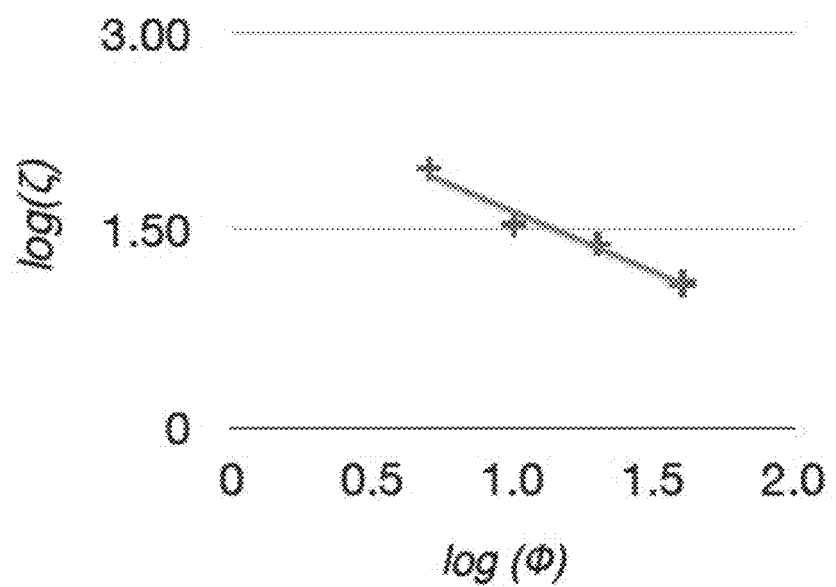
FIG. 7C is a graph of log $\xi$ as a function of log $\theta$.

Isolation of CTCs from a background of leukocytes was studied using a 30 µm pore size TEMPO filter. CTCs were labeled with Anti. CD45 MNPs and separated with the TEMPO filter (FIG. 7A). The enrichment followed the same patterns as when smaller particles and a smaller pore size was used (see FIGS. 7B and 7C).

We claim:
1. A magnetic separation device, comprising:
a membrane including a plurality of pores;
a layer of magnetically soft material adjacent the membrane; and
a passivation layer adjacent the layer of magnetically soft material;

wherein the plurality of pores extend through the layer of magnetically soft material and through the passivation layer.

2. The device of claim 1, wherein the membrane comprises a material chosen from cellulose, polymers and metal oxides.

3. The device of claim 1, wherein the membrane comprises a material chosen from polycarbonate, polyester, nylon, and aluminum oxide.

4. The device of claim 1, wherein the membrane comprises at least 1000 pores/mm$^2$.

5. The device of claim 1, wherein the plurality of pores have an average diameter ranging from about 100 nm to 100 µm.

6. The device of claim 1, wherein the plurality of pores have an average diameter ranging from about 500 nm to about 25 µm.

7. The device of claim 1, wherein the layer of magnetically soft material comprises nickel.

8. The device of claim 1, wherein the layer of magnetically soft material comprises a nickel-iron alloy.

9. The device of claim 1, wherein the passivation layer comprises nickel or gold.

10. A microfluidic device comprising:
at least one lateral flow channel; and
at least one vertical flow magnetic separation filter in fluidic communication with the at least one lateral flow channel;
wherein the at least one vertical flow magnetic separation filter comprises: (i) a membrane including a plurality of pores; (ii) a layer of magnetically soft material adjacent the membrane; and (iii) a passivation layer adjacent the layer of magnetically soft material, wherein the plurality of pores extend through the layer of magnetically soft material and through the passivation layer.

11. The microfluidic device of claim 10, further comprising a flow converter positioned between the at least one lateral flow channel and the at least one vertical flow magnetic separation filter.

12. The microfluidic device of claim 11, wherein the flow converter comprises a plurality of branching passages capable of evenly distributing fluid to the at least one vertical flow magnetic separation filter.

13. The microfluidic device of claim 10, comprising n vertical flow magnetic separation filters, wherein n=2 to 10.

14. The microfluidic device of claim 10, wherein the at least one vertical flow magnetic separation filter has a surface area of at least 0.2 cm$^2$.

15. The microfluidic device of claim 10, wherein the membrane comprises a material chosen from polycarbonate, polyester, nylon, and aluminum oxide.

16. The microfluidic device of claim 10, wherein the plurality of pores have an average diameter ranging from about 100 nm to 100 µm.

17. The microfluidic device of claim 10, wherein the layer of magnetically soft material comprises a nickel-iron alloy.

18. The microfluidic device of claim 10, wherein the passivation layer comprises nickel or gold.

19. A method for separating magnetically tagged particles, comprising:
flowing a suspension comprising the magnetically tagged particles through a magnetic separation device comprising: (i) a membrane including a plurality of pores; (ii) a layer of magnetically soft material adjacent the membrane; and (iii) a passivation layer adjacent the layer of magnetically soft material, wherein the plurality of pores extend through the layer of magnetically soft material and through the passivation layer;
capturing the magnetically tagged particles by exposing the magnetic separation device to an external magnetic field; and
releasing the magnetically tagged particles by removing the external magnetic field.

20. The method of claim 19, wherein the membrane comprises a material chosen from polycarbonate, polyester, nylon, and aluminum oxide.

21. The method of claim 19, wherein the plurality of pores have an average diameter ranging from about 100 nm to 100 µm.

22. The method of claim 19, wherein the layer of magnetically soft material comprises a nickel-iron alloy.

23. The method of claim 19, wherein the passivation layer comprises nickel or gold.

\* \* \* \* \*

UNITED STATES PATENT AND TRADEMARK OFFICE
CERTIFICATE OF CORRECTION

PATENT NO. : 11,305,280 B2
APPLICATION NO. : 16/411284
DATED : April 19, 2022
INVENTOR(S) : David Aaron Issadore et al.

It is certified that error appears in the above-identified patent and that said Letters Patent is hereby corrected as shown below:

In the Specification

Under Column 3, Line no. 5, Replace:
"FIG. 5A-5C is a schematic"
With:
-- FIGS. 5A-5C is a schematic --

Under Column 7, Line no. 1, Replace:
"a dense array (2000/mm$^2$) of"
With:
-- a dense array (~2000/mm$^2$) of --

Under Column 7, Line no. 54, Replace:
"coli and S. aureus. Fresh E. coli bacteria"
With:
-- coli and S. Aureus. Fresh E. coli bacteria --

Under Column 7, Line no. 55, Replace:
"overnight in Luria-Bertain (LB) broth"
With:
-- overnight in Luria-Bertani (LB) broth --

Under Column 8, Line no. 1, Replace:
"Scientific). S. aureus pre-labeled with Alexa"
With:
-- Scientific). S. Aureus. pre-labeled with Alexa --

Under Column 8, Line no. 2, Replace:
"Biotinylated anti-£. Coli polyclonal antibody"

Signed and Sealed this
Twelfth Day of July, 2022

Katherine Kelly Vidal
*Director of the United States Patent and Trademark Office*

Page 1 of 2

CERTIFICATE OF CORRECTION (continued)
U.S. Pat. No. 11,305,280 B2

With:
-- Biotinylated anti-E. coli polyclonal antibody --

Under Column 8, Line no. 54, Replace:
"single pore $v \propto (1-(1)-(r/a)^2)^{1/2}$ can be calculated"
With:
-- single pore $v \propto (1-(r/a)^2)^{1/2}$ can be calculated --

Under Column 10, Line no. 9, Replace:
"antibody (FIG. 6A-6C)."
With:
-- antibody (FIGS. 6A-6C). --

Under Column 10, Line no. 27, Replace:
"from the Schuykill River"
With:
-- from the Schuylkill River --

Under Column 10, Line no. 36, Replace:
"t-test), verigying that the"
With:
-- t-test), verifying that the --

Under Column 10, Line no. 40, Replace:
"from the Schuykill River"
With:
-- from the Schuylkill River --